United States Patent [19]

Merrick

[11] Patent Number: 4,883,055
[45] Date of Patent: Nov. 28, 1989

[54] ARTIFICIALLY INDUCED BLOOD PULSE FOR USE WITH A PULSE OXIMETER

[75] Inventor: Edwin B. Merrick, Stow, Mass.

[73] Assignee: Puritan-Bennett Corporation, Wilmington, Mass.

[21] Appl. No.: 167,301

[22] Filed: Mar. 11, 1988

[51] Int. Cl.$^4$ .............................................. A61B 5/00
[52] U.S. Cl. ................................. 128/633; 178/666; 600/17
[58] Field of Search ................ 128/633, 665, 6667, 128/667; 600/16, 17

[56] References Cited

U.S. PATENT DOCUMENTS

| | | | |
|---|---|---|---|
| 2,690,174 | 9/1954 | Fuchs | 128/64 |
| 3,412,729 | 11/1968 | Smith | 128/667 |
| 3,998,550 | 12/1976 | Konishi et al. | 356/39 |
| 4,077,402 | 3/1978 | Benjamin et al. | 128/64 |
| 4,086,915 | 5/1978 | Kofsky et al. | 128/2 |
| 4,167,331 | 9/1979 | Nielsen | 356/39 |
| 4,294,261 | 12/1981 | Baker et al. | 128/686 |
| 4,726,382 | 2/1988 | Boehner et al. | 128/667 |
| 4,776,339 | 10/1988 | Schreiber | 128/677 |

Primary Examiner—Kyle L. Howell
Assistant Examiner—John C. Hanley
Attorney, Agent, or Firm—Fish & Richardson

[57] ABSTRACT

An artificially induced blood pulse used for measuring oxygen saturation in arterial blood is produced by a cuff, wrapped around a body member having an artery upstream from a testing site, when a squeezing pulse is applied by the cuff to the body member.

5 Claims, 3 Drawing Sheets

ARTIFICIALLY INDUCED BLOOD PULSE FOR USE WITH A PULSE OXIMETER

BACKGROUND OF THE INVENTION

The invention relates to artifically inducing a blood pulse with a cuff for conducting blood tests with a pulse oximeter.

The existence of a blood pulse is necessary in a test for determining oxygen saturation of blood by a pulse oximeter. A typical pulse oximeter transmits light through a given area on a finger, a lobe of the ear or other blood containing body member. Infra-red and visible red light are commonly transmitted because it is known that the degree of absorption of red light is different for oxygenated vs. de-oxygenated blood and that the absorption of infra-red light is relatively insensitive to the level of oxygenation. The transmission of red and infrared light is detected by a photodiode which converts the different wavelengths of light to an electrical signal having an amplitude that is proportional to the intensities of the light transmitted. Thus, for every heartbeat, an analog signal known as a pulsatile waveform, which has maximum and minimum levels, is generated.

Using the signal generated by the infra-red light as a reference signal and the fact that tissue absorption is directly proportional to the log of the ratio of light transmitted to incident light, the percentage of oxygen saturation can be determined. The common approach for this determination is to link these signals to a computer for determining a ratio between the amplitude of the pulses for each wavelength during a heartbeat cycle. Since each ratio corresponds to a different percentage of oxygen saturation, the computer can be programmed to display from memory the percentage of oxygen saturation that corresponds to each ratio.

SUMMARY OF THE INVENTION

A general feature of the invention is that an artifically induced blood pulse is utilized by a pulse oximeter for determining oxygen saturation in the blood. The artificial pulse is generated by wrapping a cuff around a body member containing an artery, which supplies oxyhemoglobin to a capillary bed, and applying a squeezing pulse to the body member with the cuff to squeeze the artery.

Preferred embodiments of the invention include the following features. The cuff comprises an envelope for storing pressurized air and a tube for introducing and exhausting the pressurized air into and out of the envelope. The artificial blood pulse is synchronized with a normal blood pulse and is utilized by a pulse oximeter which may be adjacent to the cuff.

Another general feature of the invention is that muscles are electrically stimulated to artificially induce blood pulses.

Preferred embodiments of the invention include electrodes placed on the side of a finger or an arm for transmitting electrical pulses which cause muscles to contract. Contractions may be controlled by a multi-function patient monitor, which generates electrical pulses in synchronism with a normal blood pulse.

An advantage of the invention is that artificial pulses can replace normal blood pulses which are too weak utilization by devices such as a pulse oximeter.

Other advantages and features will become apparent from the following description of the preferred embodiment and from the claims.

DESCRIPTION OF THE PREFERRED EMBODIMENT

The drawings are briefly described as follows.

STRUCTURE

Figure 1:
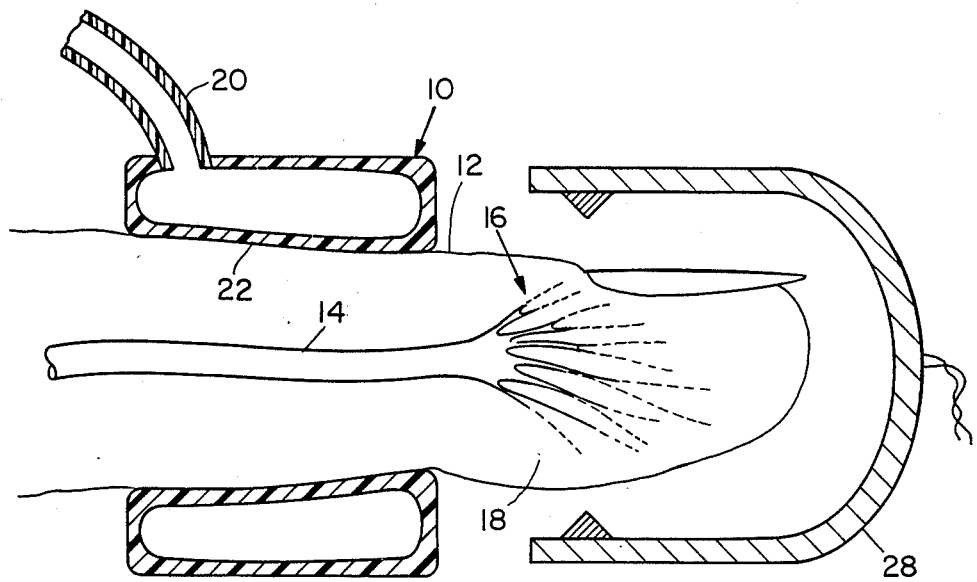
FIG. 1 is a cross-sectional schematic diagram illustrating the use of a finger cuff and a finger pulse oximeter probe.
Figure 2:
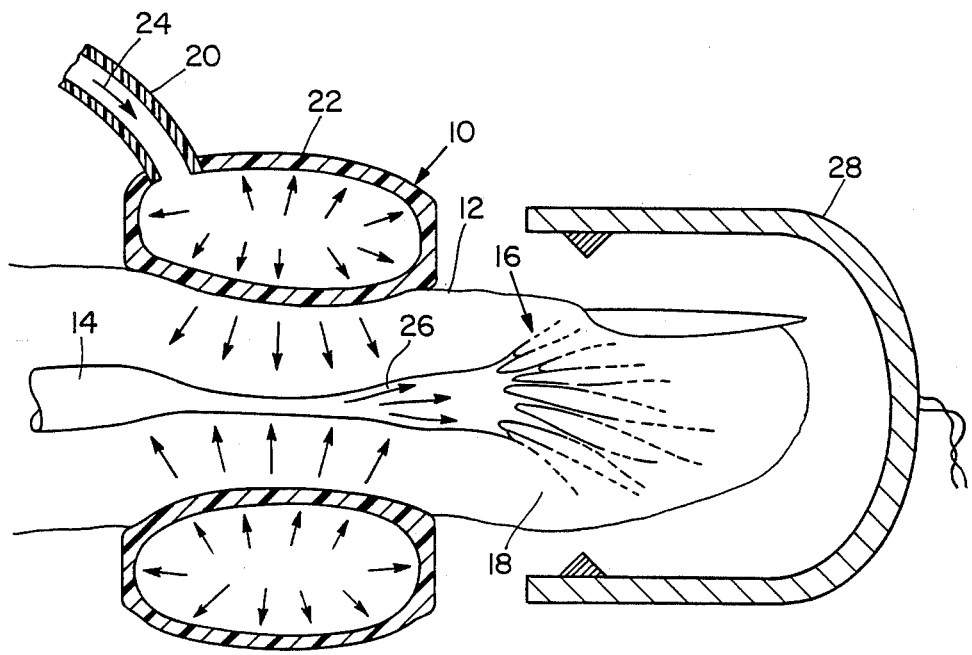
FIG. 2 is a cross-sectional schematic diagram illustrating the action of an inflated cuff on an artery feeding a capilliary bed.

Referring to FIGS. 1 and 2 a finger cuff 10 is placed firmly around a finger 12 for the purpose of compressing an artery 14 feeding a capillary 16 bed in the finger tip 18. The cuff 10 may be made from a plastic material formed to create an inflatable envelope 22. A tube 20 extending from the envelope 22 allows a pulse of air to be pumped into or out of the envelope 22. As air is pumped into the envelope, sufficient pressure is applied by the sides of the envelope 22 to squeeze the finger 12 and the artery 14. A progressive artery compression with an associated volume displacement of the artery will launch a pressure wave toward the capillary bed 16. This surge of blood is larger than a surge created by a normal pulse thereby improving the performance of a pulse oximeter probe 28. The amount and duration of pressure applied to the finger may be controlled to synchronize with normal blood pulse.

Figure 3:
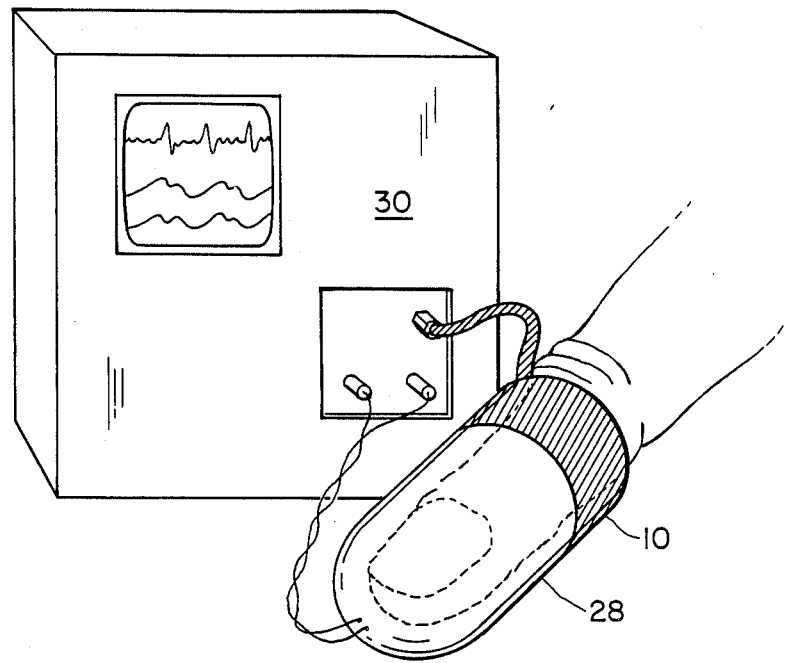
FIG. 3 is a perspective schematic diagram illustrating a finger cuff and an oximeter probe as an intergral unit.

Referring to FIG. 3, the cuff 10 and the pulse oximeter probe 28 may be made into one integral unit and controlled by a multi-function patient monitor 30 such that an electro-cardiogram signal may be used as a synchronization source to trigger the applied pressure pulse driving the cuff.

Figure 4:
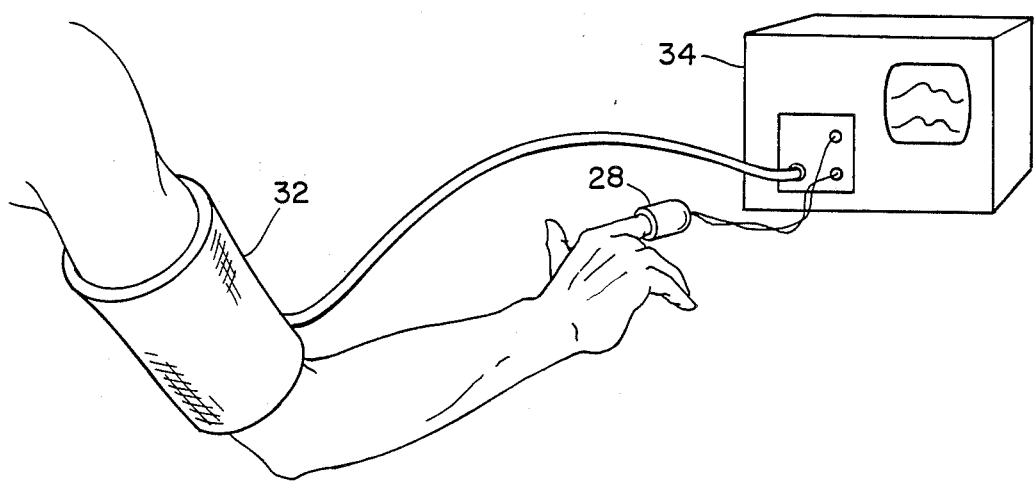
FIG. 4 is a perspective schematic diagram illustrating the use of an arm cuff and a finger pulse oximeter probe.

In an alternate embodiment, artifically induced blood pulses are generated by an arm cuff 32, similar to a blood pressure cuff, wrapped around the patient's arm (FIG. 4) Detection of artificial pulses are made by the finger pulse oximeter probe 28. Both the arm cuff and the probe are operated by a common instrument 34.

Figure 5:
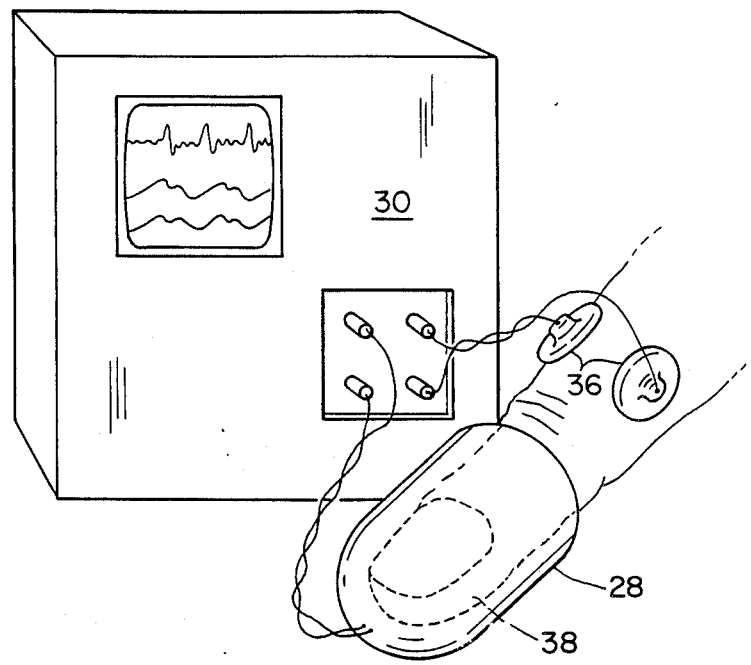
FIGS. 5 and 6 are perspective schematic diagrams illustrating the use of electrodes for stimulating muscle contractions for generating artificially induced blood pulses.
Figure 6:
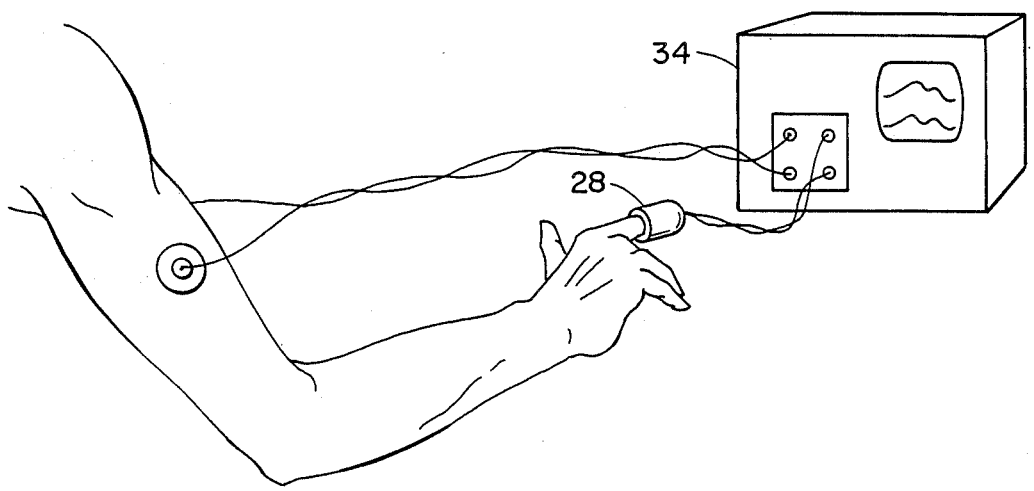

As shown in FIGS. 5 and 6 in an another alternate embodiment, electrical stimulation may be used to contract muscles for artificially inducing blood pulses. Electrodes 36 placed on the sides of a finger 38 (FIG. 5) or an arm (FIG. 6) may be controlled by the multi-function patient monitor 30 to contract muscles in synchronism with normal blood pulses. With each contraction, a surge of blood is launched toward the capillary bed.

Other embodiments are within the following claims.

1. A pulse oximeter for determining oxygen saturation comprising:
   a means for transmitting at least two wavelengths of light related to hemoglobin light absorption through a body member;
   a cuff means for artificially inducing blood pulse in the body member;

photodetection means for detecting light transmitted through said body member and for producing electrical signals that are proportional to intensities of light detected for each wavelength of light; and electronic means for receiving the electronic signals produced by the photodetection means when blood is pulsed in said body member by said cuff means for determining oxygen saturation.

2. A pulse oximeter in accordance with claim 1 wherein the cuff means comprises:

an inflatable envelope; and a tube interconnected with the inflatable envelope and adapted for introducing and exhausting air into and out of said envelope.

3. The pulse oximeter of claim 1 wherein the blood pulse is applied in synchronism with normal blood pulses.

4. The pulse oximeter of claim 1 wherein the cuff means is a finger cuff.

5. The pulse oximeter of claim 1 wherein the cuff means is an arm cuff.

* * * * *

UNITED STATES PATENT AND TRADEMARK OFFICE
CERTIFICATE OF CORRECTION

PATENT NO. : 4,883,055
DATED : November 28, 1989
INVENTOR(S) : Edwin B. Merrick

It is certified that error appears in the above-identified patent and that said Letters Patent is hereby corrected as shown below:

Column 1, line 67: after the word "weak" add -- for --.

Signed and Sealed this

Fifth Day of February, 1991

Attest:

HARRY F. MANBECK, JR.

*Attesting Officer*  *Commissioner of Patents and Trademarks*